United States Patent
Silver et al.

(10) Patent No.: US 9,874,565 B2
(45) Date of Patent: Jan. 23, 2018

(54) ONCOGENE ASSOCIATED WITH HUMAN CANCERS AND METHODS OF USE THEREOF

(71) Applicant: Dana-Farber Cancer Institute, Inc., Boston, MA (US)

(72) Inventors: Daniel P. Silver, Wayland, MA (US); Manish Neupane, Watertown, MA (US); David E. Hill, Somerville, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/900,606

(22) PCT Filed: Jun. 23, 2014

(86) PCT No.: PCT/US2014/043701
§ 371 (c)(1),
(2) Date: Dec. 21, 2015

(87) PCT Pub. No.: WO2014/205445
PCT Pub. Date: Dec. 24, 2014

(65) Prior Publication Data
US 2016/0139127 A1    May 19, 2016

Related U.S. Application Data

(60) Provisional application No. 61/837,952, filed on Jun. 21, 2013.

(51) Int. Cl.
| | | |
|---|---|---|
| *C12N 15/11* | (2006.01) | |
| *G01N 33/574* | (2006.01) | |
| *C12Q 1/68* | (2006.01) | |
| *C12N 15/10* | (2006.01) | |
| *C12N 15/113* | (2010.01) | |

(52) U.S. Cl.
CPC ..... *G01N 33/5748* (2013.01); *C12N 15/1086* (2013.01); *C12N 15/1135* (2013.01); *C12Q 1/6886* (2013.01); *C12N 2310/14* (2013.01); *C12N 2310/531* (2013.01); *C12N 2320/30* (2013.01); *G01N 2333/4703* (2013.01)

(58) Field of Classification Search
None
See application file for complete search history.

(56) References Cited

U.S. PATENT DOCUMENTS

| 7,662,778 B2 * | 2/2010 | Yoshida | C07K 5/126 514/1.1 |
|---|---|---|---|
| 2012/0004132 A1 * | 1/2012 | Zhang | C12Q 1/682 506/9 |

OTHER PUBLICATIONS

Gros et al. Biochimie 94 2012, 2280-2286.*
Fang et al. World J Gastroenterol 2004;10:3394-3398.*
Bernard D et al: The methyl-CpG-binding protein MECP2 is required for prostate cancer cell growth.:, Oncogene Mar. 2, 2006, vol. 25, No. 9, Mar. 2, 2005 (Mar. 2, 2006), pp. 1358-1366, XP002732003, ISSN: 0950-9232 the whole document.
Karst Alison M et al.: Modeling high-grade serous ovarian carcinogenesis from the fallopian tube.:, Proceeding of the National Academy of Sciences of the United States of America May 3, 2011, vol. 108, No. 18, May 3, 2011 (May 3, 2011), pp. 7547-7552, XP002732004, ISSN: 1091-6490 the whole document.
Yaqinuddin Ahmed et al: Silencing of MBD1 and MeCP2 in prostate-cancer-derived PC3 cells produces differential gene expression profiles and cellular phenotypes.:, Bioscience Reports Dec. 2008, vol. 28, No. 6, Dec. 2008 (Dec. 2008), pp. 319-326., XP002732005, ISSN: 0144-8463 the whole document.
Chavez KJ et al: "Triple negative breast cancer cell lines: one tool in the search for better treatment of triple nragtive breasat cancer", Internet Citation, 2010, pp. 1-17, XP002712389, Retrieved from the Internet: URL:http://www.ncbi.nlm.nih.gov/pmc/articles/PMC3532890/ [retrieved on Sep. 16, 2013] the whole document.
Federica Babbio et al: "Knock-down of methyl Cpg-binding protein 2 (meCP2) causes alterations in cell proliferation and nuclear lamins expression in mammalian cells", BMC Cell Biology, Biomed Central, London, GB, vol. 13, No. 1, Jul. 11, 2012 (Jul. 11, 2012), p. 19, XP021106618, ISSN: 1471-2121, DOI: 10.1189/1471-2121-13-19 the whole document.
Internation Search Report and Written Opinion issued for International Application No. PCT/US2014/043701 dated Nov. 5, 2014 and mailed Nov. 21, 2014, 11 pages.
Adamson, David C et al. "Otx2 is critical for the maintenance and progression of Shh-independent medulloblastomas", *Cancer Res*, 70(1):181-91, Jan. 2010.
Boon, Kathy et al. "Genomic amplification of orthodenticle homologue 2 in medulloblastomas", *Cancer Research*, 65(3):703-707, Feb. 2005.
Chahrour, Maria et al. "Mecp2, a key contributor to neurological disease, activates and Represses transcription", *Science*, 320(5880): 1224-9, May 2008.
Elenbaas, B et al. "Human breast cancer cells generated by oncogenic transformation of primary mammary epithelial cells", *Genes & Development*, 15(1):50-65, 2001.
Guy et al, "The Role of MeCP2 in the Brain", *Annual Review Cell Dev. Biol.*, p. 631-652, 2011.

(Continued)

*Primary Examiner* — Brian A Whiteman
(74) *Attorney, Agent, or Firm* — Cooley LLP; Ivir R. Elrifi; Cynthia A. Kozakiewicz

(57) ABSTRACT

The present invention provides methods of treating cancer by inhibiting MECP2 and identifying cancers that will respond to therapy using MECP2 as a biomarker.

6 Claims, 24 Drawing Sheets

(56) References Cited

OTHER PUBLICATIONS

Hahn, W C et al. "Creation of human tumour cells with defined genetic elements", *Nature*, 400(6743):464-468, Jul. 1999.

Ince, Tan A et al. "Transformation of different human breast epithelial cell types leads to distinct tumor phenotypes", *Cancer Cell*, 12(2):160-170, Aug. 2007.

Jordan, ChaRandle et al. "Cerebellar gene expression profiles of mouse models for Rett syndrome reveal novel MeCP2 targets", *BMC Medical Genetics*, 8:36, 2007.

Lopez-Serra et al. "Proteins that bind methylated DNA and human cancer: reading the wrong words", *British Journal of Cancer*, 98, p. 1881-1885, 2008.

Mellen, Marian et al. "Mecp2 binds to 5hmc enriched within active genes and accessible chromatin in the nervous system", *Cell*, 151(7):1417-30, Dec. 2012.

Muller, H. et al. "MeCP2 and MBD2 expression in human neoplastic and non-neoplastic breast tissue and its association with oestrogen receptor status", British Journal of Cancer, vol. 89, p. 1934-1939, 2003.

Nan, X et al. "Transcriptional repression by the methyl-CpG-binding protein MeCP2 involves a histone deacetylase complex", *Nature*, 393(6683):386-389, May 1998.

Yang, Xiaoping et al. "A public genome-scale lentiviral expression library of human ORFs", *Nat Methods*, 8(8):659-61, Aug. 2011.

* cited by examiner

FIG.2

(n-1) screen

Colony forming ability in soft agar as a surrogate assay for tumorigenic transformation (n) genetic elements = hTERT+SV40-LT+SV40-st+H-Ras$^{v12}$
Primary MECs + (n) genetic elements = Transformed cells
Primary MECs + (n-1) genetic elements = Non-transformed cells

| Primary cells + (n-1) combination | Missing components |
|---|---|
| hTERT+SV40-LT+SV40-st | H-Ras$^{v12}$ |
| hTERT+SV40-LT+H-Ras$^{v12}$ | SV40-st |
| hTERT+SV40-st+H-Ras$^{v12}$ | SV40-LT |
| SV40-LT+SV40-st+H-Ras$^{v12}$ | hTERT |

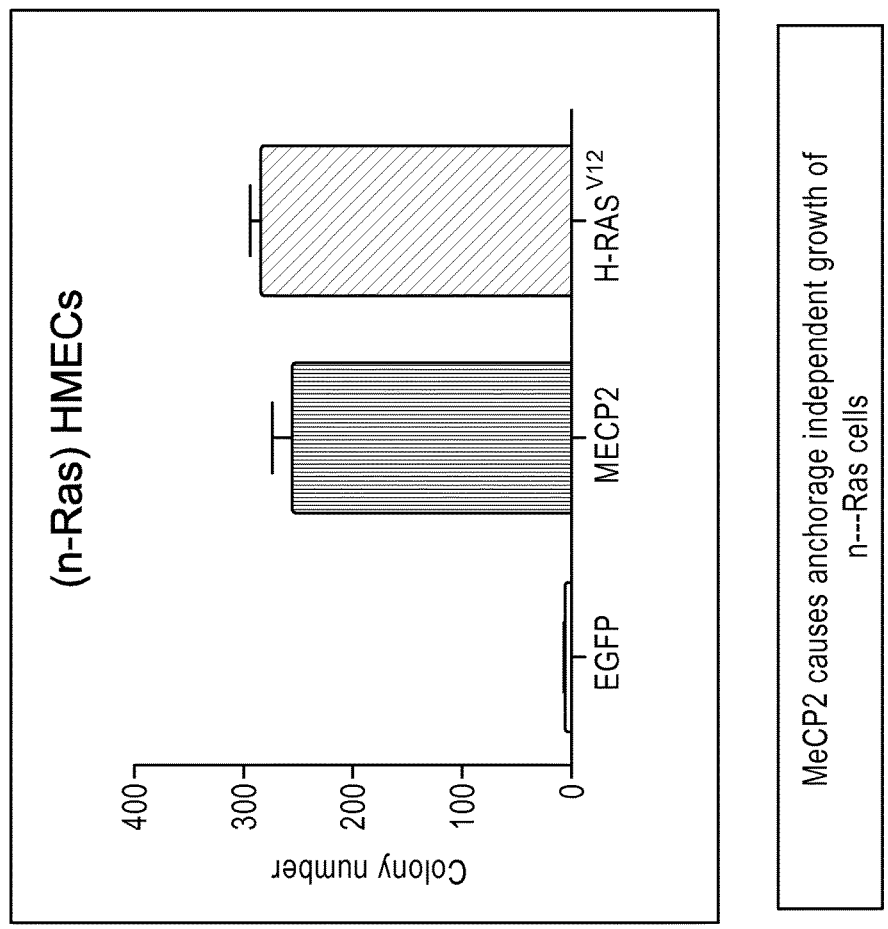

FIG.5

Methyl-CpG binding Protein 2 (MECP2)

- Nuclear protein that binds methylated DNA
- Global epigenetic regulator of gene expression
  - through recruitment of histone modifying and chromatin remodeling complexes
- Conventional role:
  - Transcriptional repressor
- Emerging role:
  - multifunctional protein
    - Positive regulator of transcription
    - RNA splicing & chromatin architecture

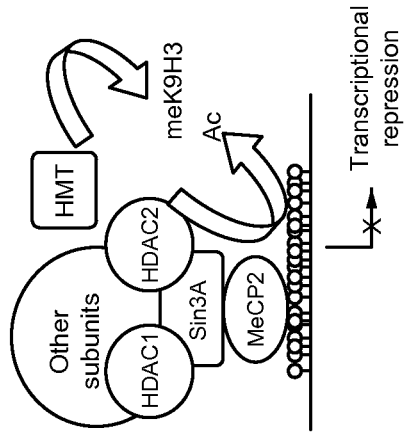

FIG.6
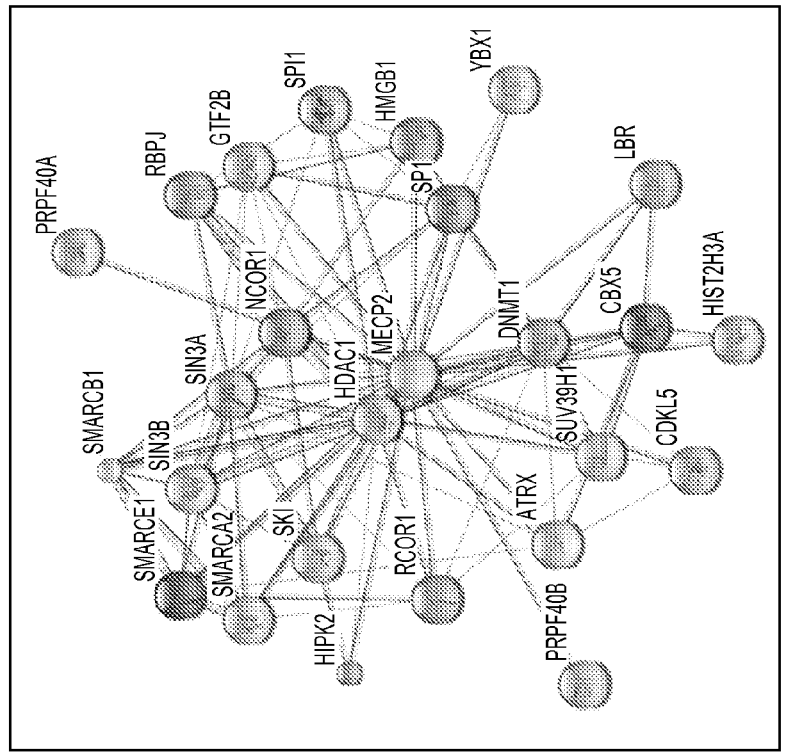

FIG.7

MECP2 amplification in cancers

L Summary Amplifications Deletions
MECP2 (chr23: 152940457-153016382)

| Cancer Subset | In Peak? | Nearest Peak | #Genes in Peak | Q-value | Frequency of Amplification | | |
|---|---|---|---|---|---|---|---|
| | | | | | Overall | Focal | High-level |
| all epithelial | Yes | chr23: 152820884-154569169 | 53 | 3.7E-16 | 0.2009 | 0.0671 | 0.0192 |
| all lungT'ES | Yes | chr23: 152820884-154569169 | 53 | 3.44E-10 | 0.2459 | 0.0807 | 0.0202 |
| Lung NSC | Yes | chr23 152720129-154569169 | | 2.06E-7 | 0.2855 | 0.093 | 0.0245 |
| all hematologic | Yes | chr23 152720129-154569169 | 58 | 2.72E-7 | 0.2865 | 0.0928 | 0.0259 |
| Acute lymphoblastic leukemia | Yes | chr23 152094405-154569169 | 71 | 4.25E-6 | 0.1202 | 0.0386 | 0.0143 |
| | | chr23 130582441-154569169 | 192 | 6.56E-5 | 0.1586 | 0.0486 | 0.0153 |
| Colorectal | Yes | chr23: 122966258-154569169 | 217 | 0.293 | 0.2387 | 0.1193 | 0.0288 |
| | | chr23: 148267454-148753845 | 9 | 0.0877 | 0.1801 | 0.0559 | 0.0124 |
| all neural | No | No peak on chromosome | 0 | 0.58 | 0.1152 | 0.0276 | 0.0092 |
| Renal | No | chr23: 153531195-154569169 | 33 | 0.772 | 0.0952 | 0.0238 | 0.0079 |
| Hepatocellular | No | chr23: 14236816-19468566 | 33 | 0.851 | 0.3306 | 0.0331 | 0.0083 |
| Lung SC | No | No peak on chromosome | 0 | 0.985 | 0.275 | 0.1 | 0.0 |
| Medulloblastoma | No | No peak on chromosome | 0 | 0.99 | 0.1094 | 0.0234 | 0.0078 |
| Esophageal squamous | No | No peak on chromosome | 0 | 1.0 | 0.5 | 0.0909 | 0.0455 |
| Myeloproliferative disorder | No | No peak on chromosome | 0 | 1.0 | 0.014 | 0.0047 | 0.0 |
| Ovarian | No | chr23: 42189356-90472515 | 276 | 1.0 | 0.2039 | 0.0777 | 0.0097 |
| Glioma | No | No peak on chromosome | 0 | 1.0 | 0.122 | 0.0488 | 0.0244 |

FIG.8
Likely Significant Amplification in GYN Cancers as well

| Cancer Subset | In Peak? | Nearest Peak (click link to launch IGV) | #Genes in Peak | Q-value | Frequency of Amplification | | |
|---|---|---|---|---|---|---|---|
| | | | | | Overall | Focal | High-level |
| all cancers | Yes | chrX: 152980865-153781435 | 74 | 6.89E-12 | 0.1776 | 0.0721 | 0.0185 |
| Epithelial cancers | Yes | chrX: 152984594-153624197 | 27 | 1.06E-11 | 0.1931 | 0.0789 | 0.0199 |
| Lung adenocarcinoma | Yes | chrX: 151843349-154905589 | 104 | 2.43E-6 | 0.3027 | 0.1514 | 0.0323 |
| Lung cancers | Yes | chrX: 152699719-154905589 | 104 | 3.6E-6 | 0.272 | 0.1314 | 0.0289 |
| Ovarian serous cystadenocarcinoma | Yes | chrX: 152840382-154905589 | 82 | 9.76E-6 | 0.381 | 0.2272 | 0.0787 |
| Uterine corpus endometrioid carcinoma | Yes | chrX: 153029079-153383539 | 18 | 0.0488 | 0.1667 | 0.063 | 0.0142 |
| Cervical squamous cell carcinoma | Yes | chrX: 137484325-154905589 | 206 | 0.057 | 0.2807 | 0.1667 | 0.0263 |
| Lung squamous cell carcinoma | Yes | chrX: 148623455-154905589 | 142 | 0.17 | 0.2374 | 0.1089 | 0.0251 |

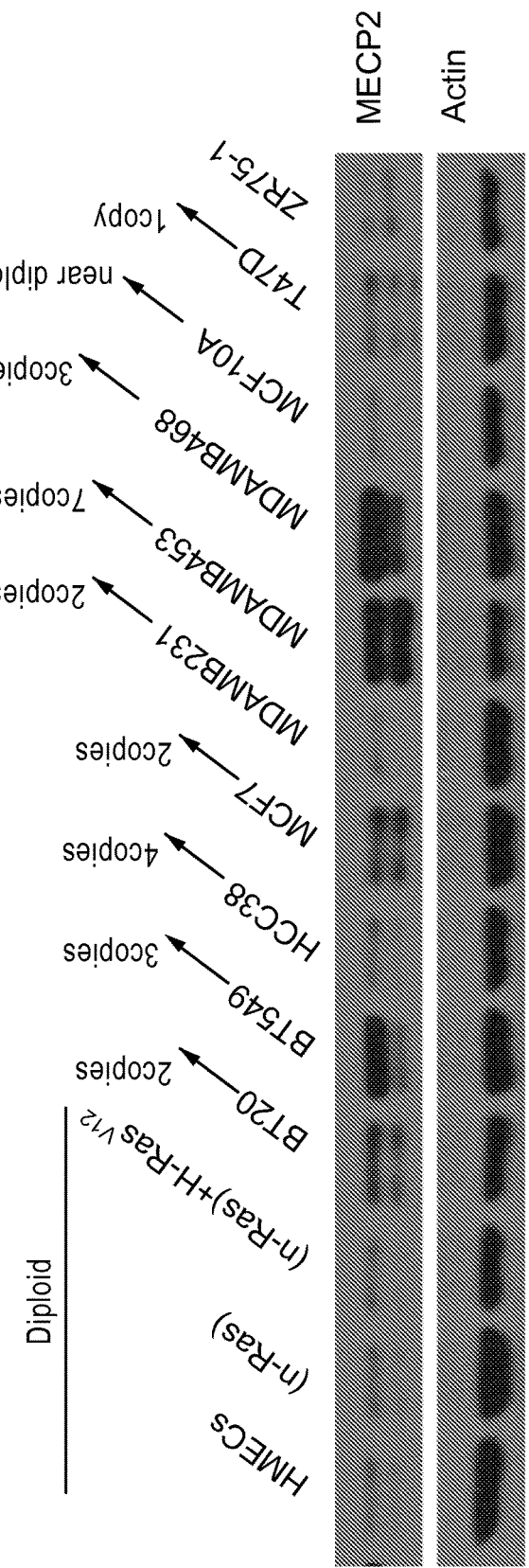
FIG.9 MeCP2 expression across breast cancer cell lines

Mutations in MECP2 that fail to transform also do not activate the MAPK pathway

ONCOGENE ASSOCIATED WITH HUMAN CANCERS AND METHODS OF USE THEREOF

RELATED APPLICATIONS

This application is a national stage application filed under 35 U.S.C. §371, of International Application No. PCT/US14/43701, filed on Jun. 23, 2014 which claims priority to and the benefit of U.S. provisional application no. 61/792,336 filed Jun. 21, 2013, the contents of which are hereby incorporated by reference in its entirety.

FIELD OF THE INVENTION

The present invention relates generally to the identification of MECP2 as an oncogene, methods of using such MECP2 in determining the response to therapy and treating cancer by inhibiting MECP2.

SUMMARY OF THE INVENTION

In various aspects the invention features methods of predicting whether a tumor will respond to a cancer therapy by determining whether MECP2 is amplified or overexpressed in the tumor. Amplification or overexpression indicates the tumor will respond to therapy. The MECP2 is the MECP2 long isoform, the MECP2 short isoform or both. The cancer therapy is an epigenetic therapy such as a DNA methylation inhibitor or a histone deacetylation (HDAC) inhibitor. DNA methylation inhibitors include for example 5-azacytidine or decitabine. When the MECP2 long isoform is overexpressed it indicates that the subject will respond to a phosphoinositide 3-kinase (PI3K) inhibitor. When the MECP2 short isoform is overexpressed it indicated that the subject will respond to a MAP kinase inhibitor.

In some aspects the cancer therapy is a MECP2 inhibitor such as a nucleic acid that inhibits MECP2 expression or activity. A nucleic acid that inhibits MECP2 expression or activity includes for example a nucleic acid that is complementary to a MECP2 nucleic acid or fragment thereof. The cancer therapy is a MEK inhibitor, a phosphoinositide 3-kinase (PI3K) inhibitor, a c-myc inhibitor, or a tyrosine kinase inhibitor.

Also included in the invention are methods of treating subject with a tumor having an MECP2 amplification or overexpression of MCEP2 by administering to the subject a MECP2 inhibitor, a DNA methylation inhibitor a histone deacetylation (HDAC) inhibitor, a MEK inhibitor, a phosphoinositide 3-kinase (PI3K) inhibitor, a c-myc inhibitor, a tyrosine kinase inhibitor or any combination thereof. When the MECP2 long isoform is overexpressed a subject is treated with a a phosphoinositide 3-kinase (PI3K) inhibitor. When the MECP2 short isoform is present the subject is treated with a MAP kinase inhibitor.

In a further aspect the invention provides a method of identifying a gene capable of tumorigenic transformation by providing a primary cell culture transformed with three of the following genetic elements: telomerase; SV40 large-T antigen; SV40 small-T antigen or RAS and contacting the cell culture with an expression library of human protein-coding sequences. Genes capable of tumorigenic transformation are identified by determining what human protein sequence when expressed in the cell allows for anchorage independent growth.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 2 illustrates the screen according to the invention

FIG. 4 shows that MECP2 causes anchorage independent growth in n-RAS cells.

FIG. 5 summarizes the functions of MECP2.

FIG. 6 illustrates MECP2 protein interactions.

FIG. 7 summarizes MECP2 amplifications in cancer.

FIG. 8 shows MECP2 amplification in gynecological cancers.

FIG. 9 shows MEPC2 expression in breast cancers.

DETAILED DESCRIPTION OF THE INVENTION

Figure 1:
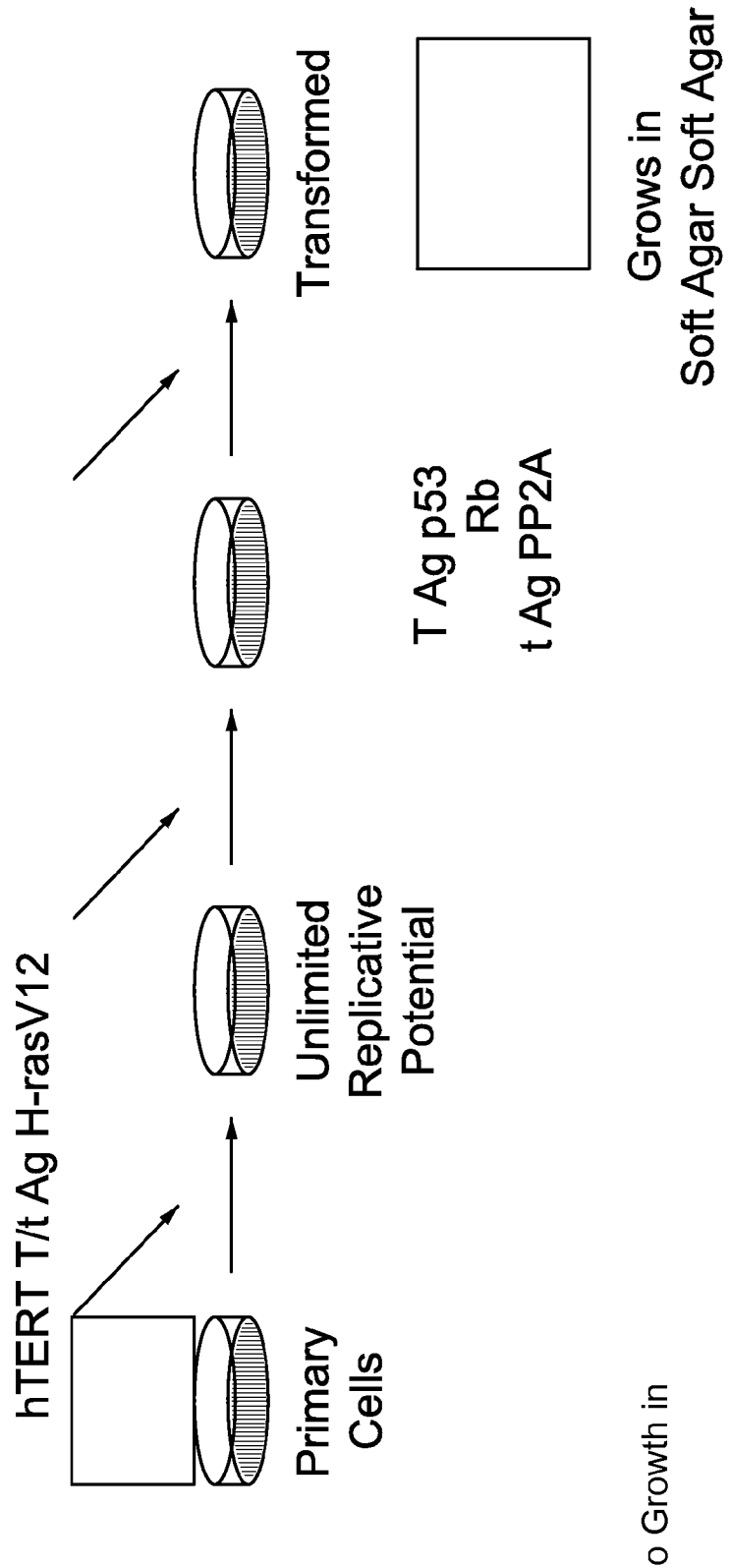
FIG. 1 illustrates the experimental transformation of primary cells.
Figure 3:
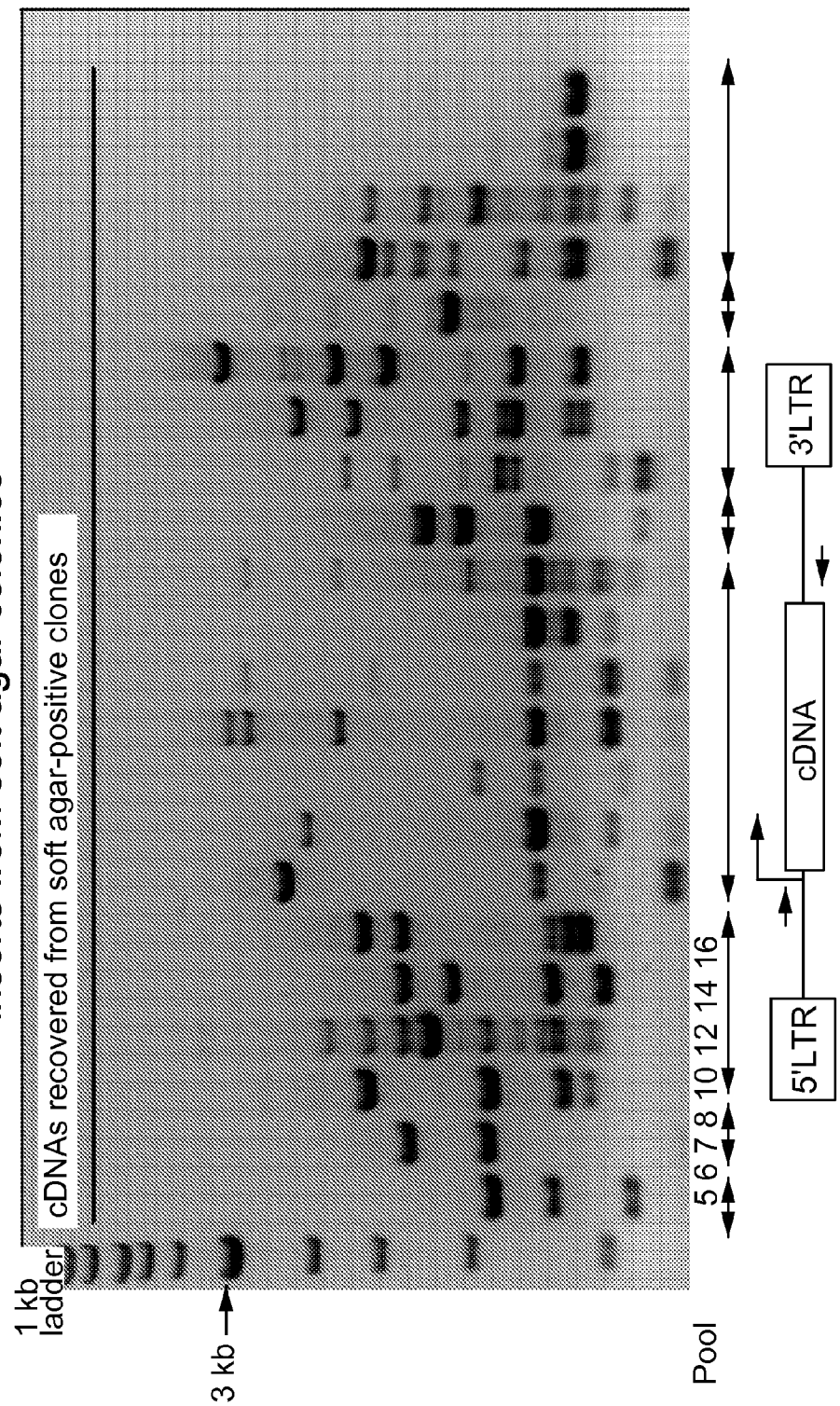
FIG. 3 is a photograph of PCT amplification of cDNA inserts form soft agar colonies.
Figure 10:
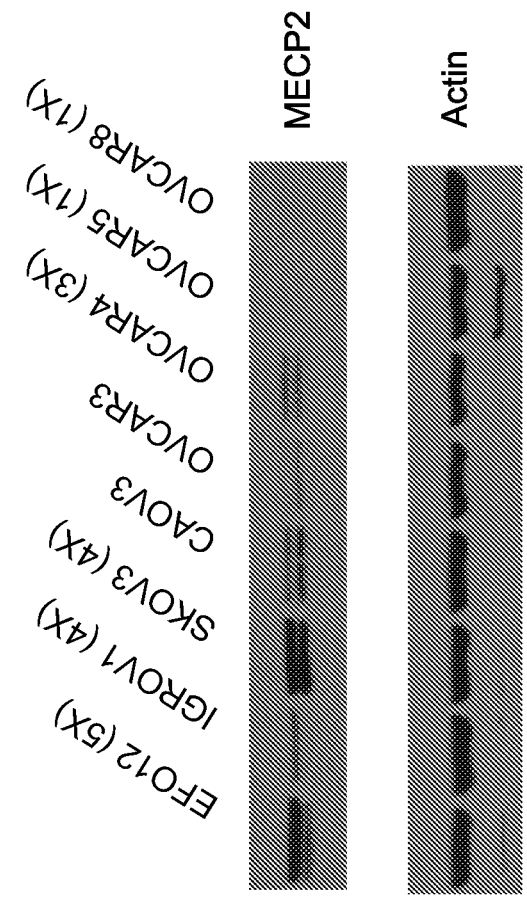
FIG. 10 shows MEPC2 expression in ovarian cell lines
Figure 11:
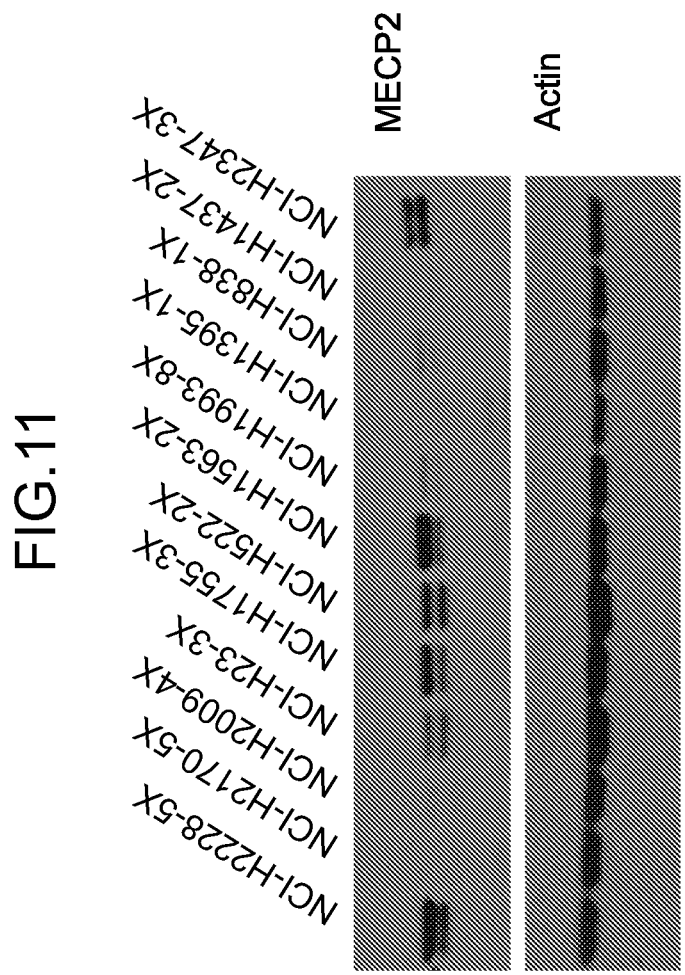
FIG. 11 shows MEPC2 expression in non-small cell lung cancer cell lines.
Figure 12:
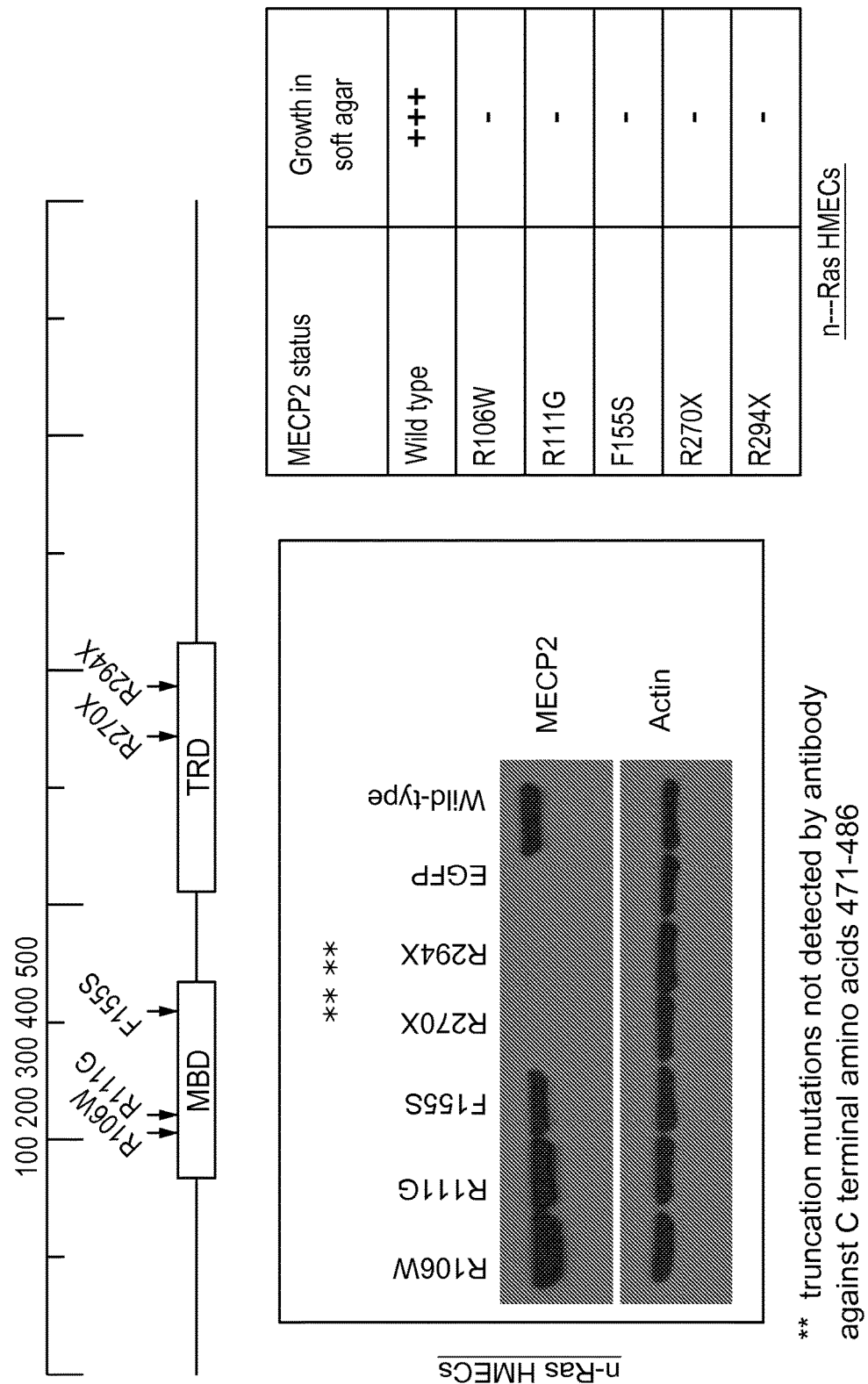
FIG. 12 illustrates the effect of loss of function point mutation in transformation potential of MECP2.
Figure 13:
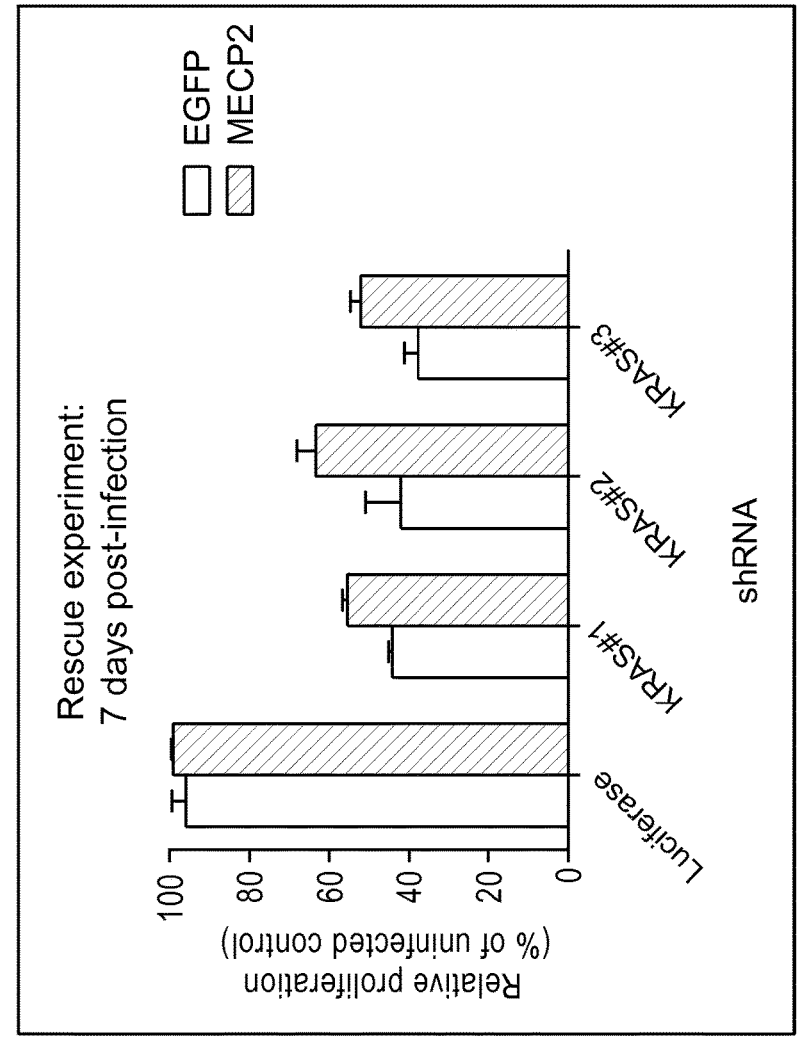
FIG. 13 shows that MECP2 partially rescues cytotoxic and anti-proliferative effects of RAS suppression in a human tumor cell line
Figure 14:
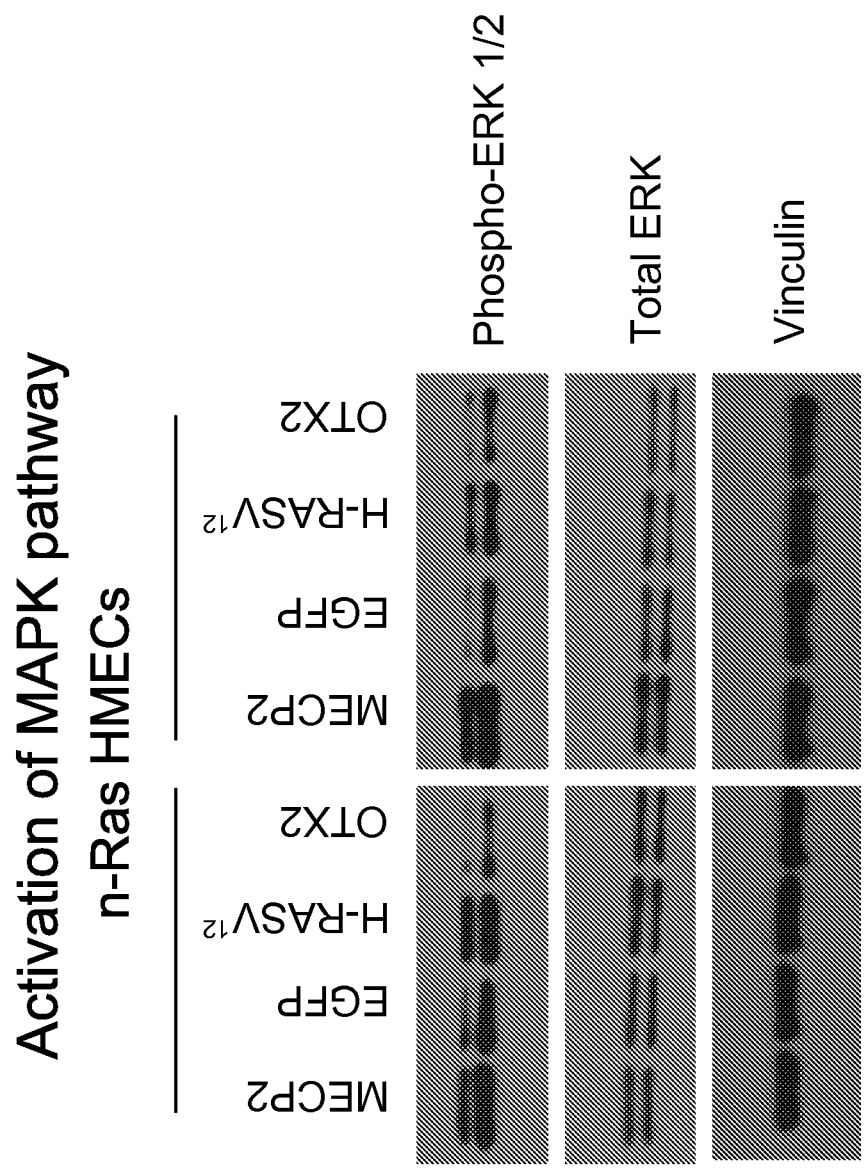
FIG. 14 shows that MECP2 activates MAP kinase pathway.
Figure 15:
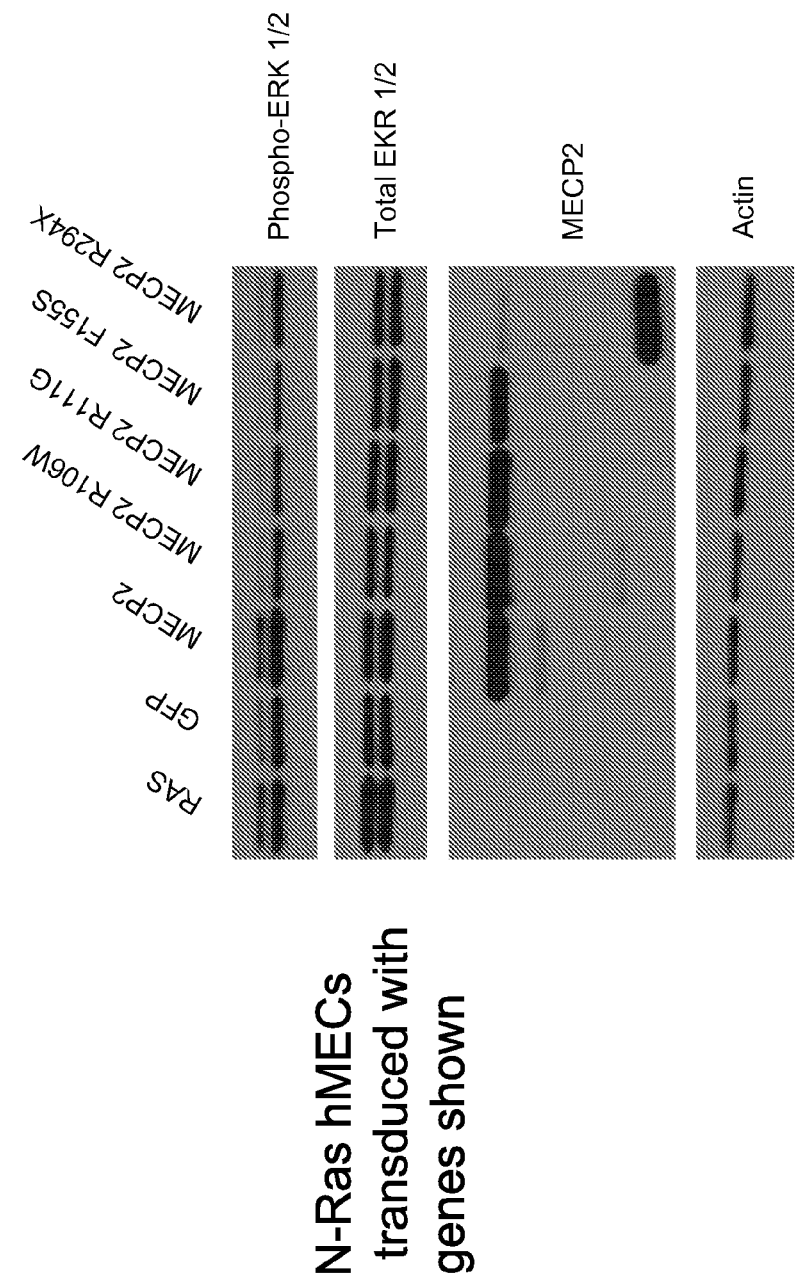
FIG. 15 illustrates that mutation in MECP2 that fail to transform also do not activate MAPK pathway
Figure 16:
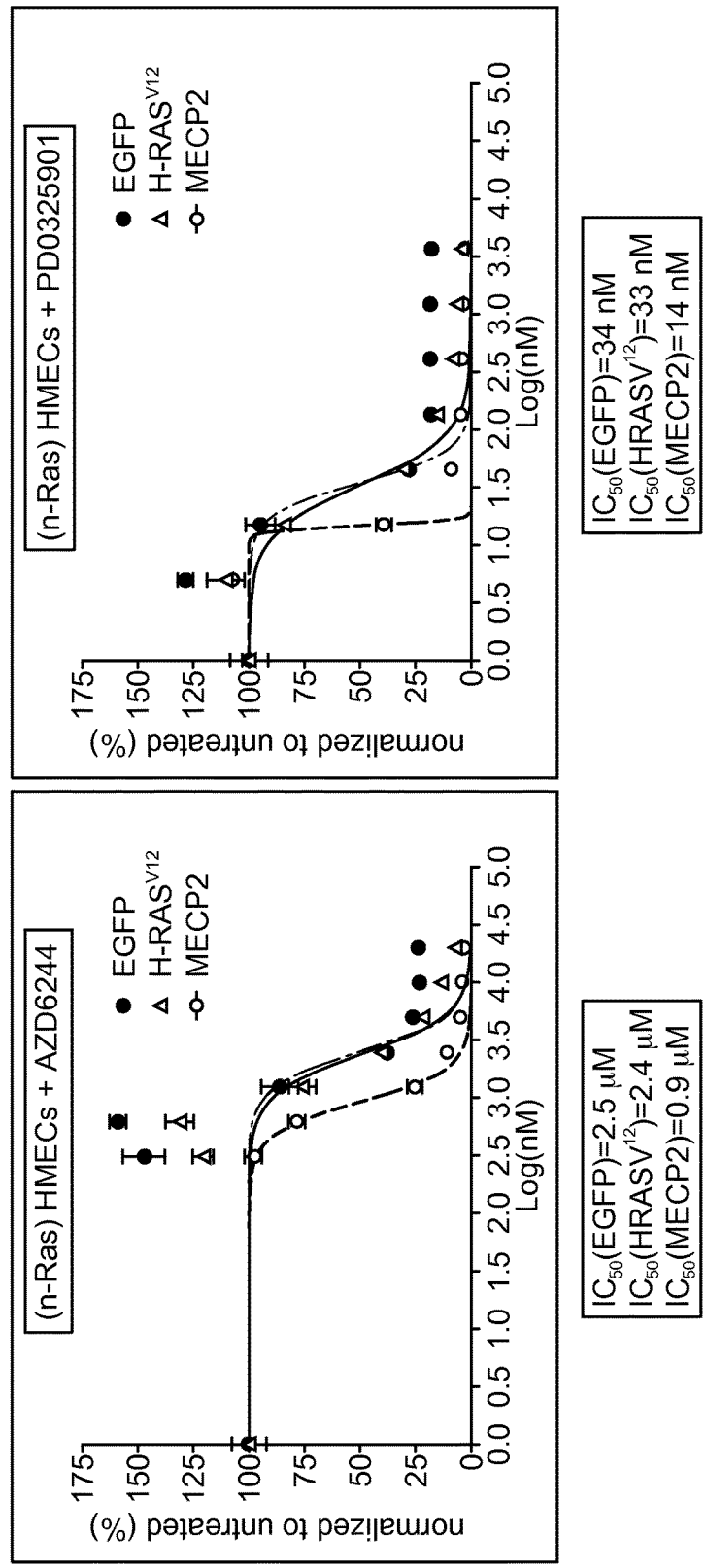
FIG. 16 shows response to MEK inhibitors.
Figure 17:
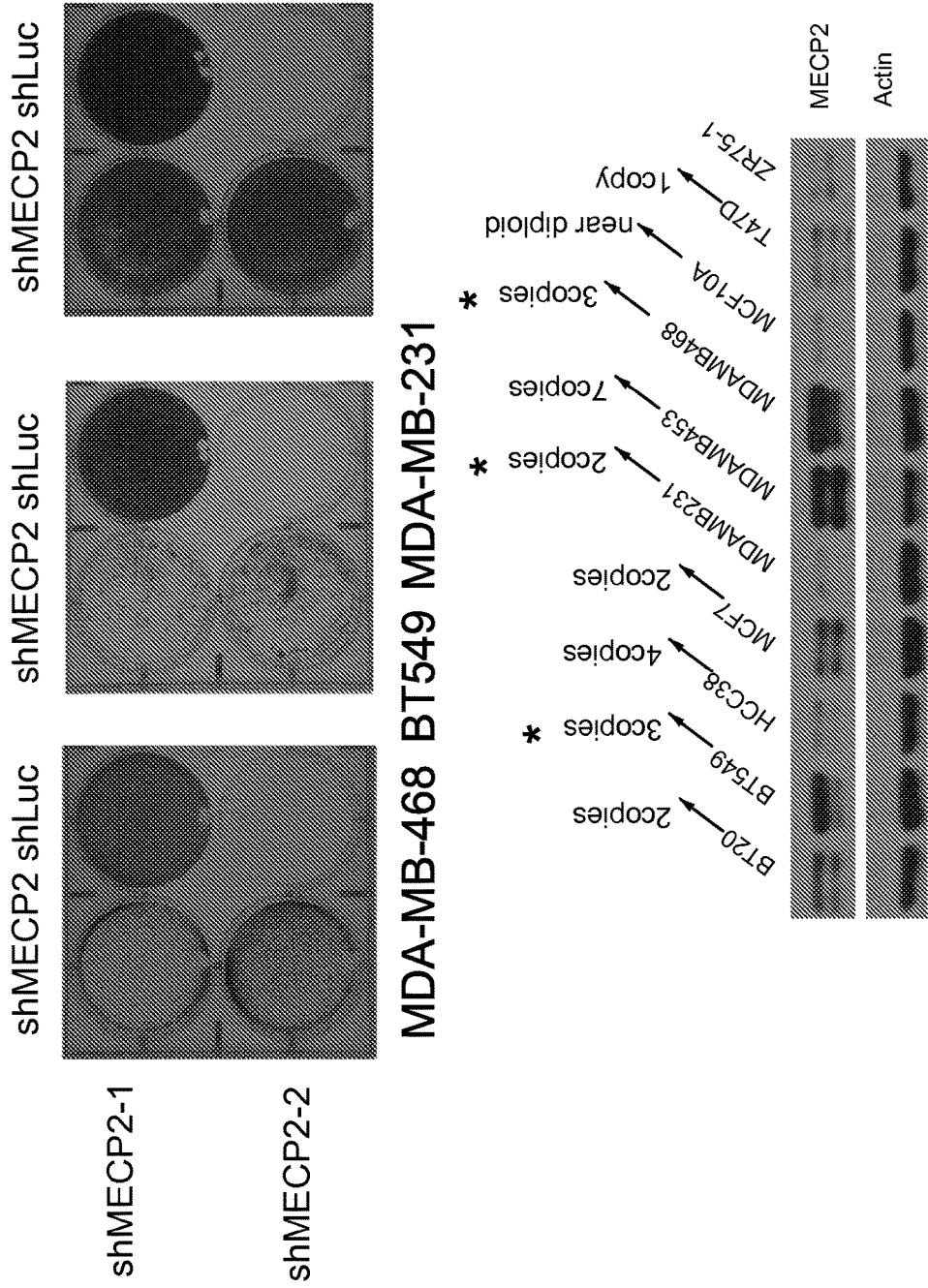
FIG. 17 illustrates that some breast tumor lines depend on MECP2 for growth.
Figure 18:
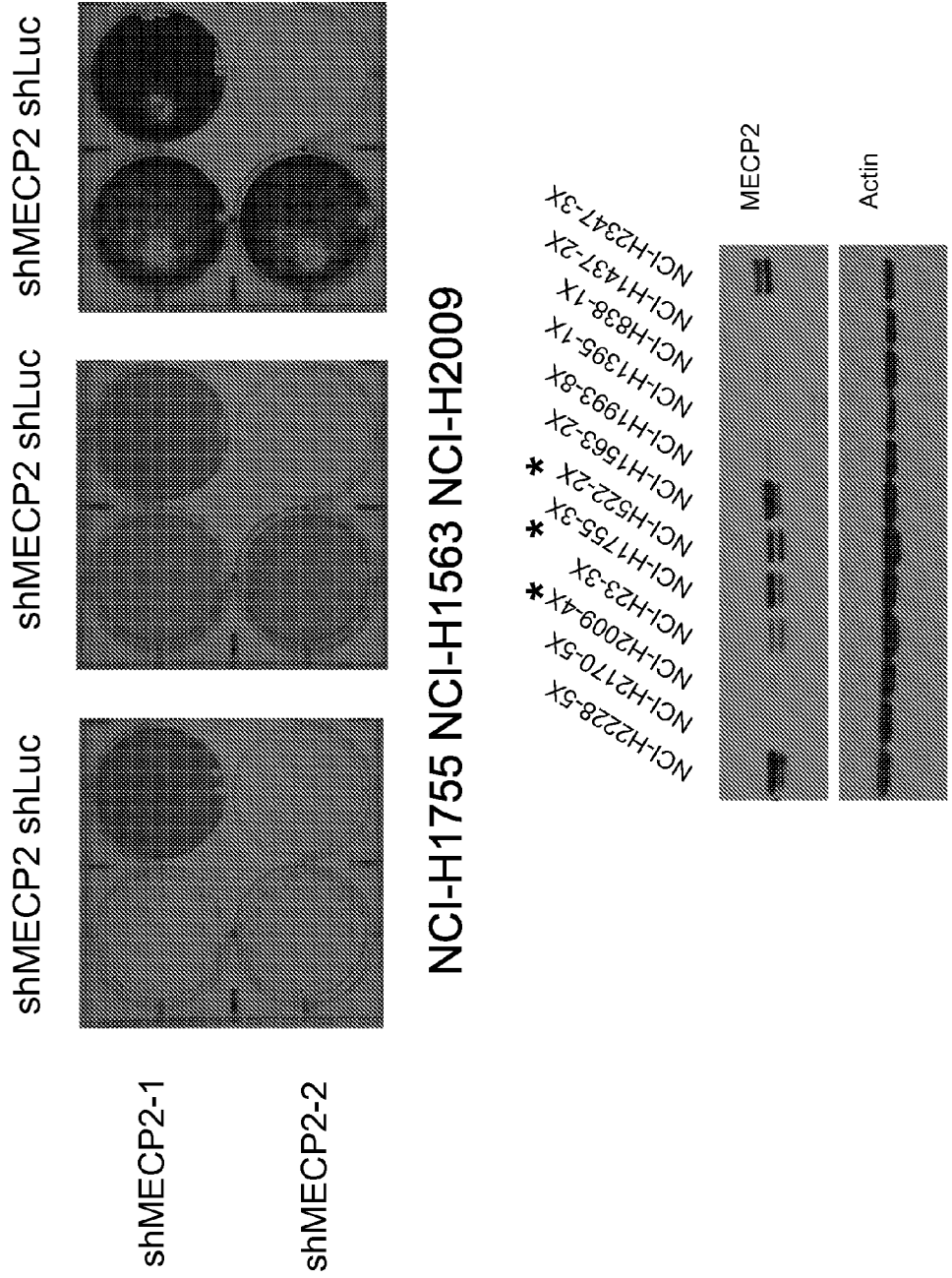
FIG. 18 illustrates that some lung tumor lines depend on MECP2 for growth.
Figure 19:
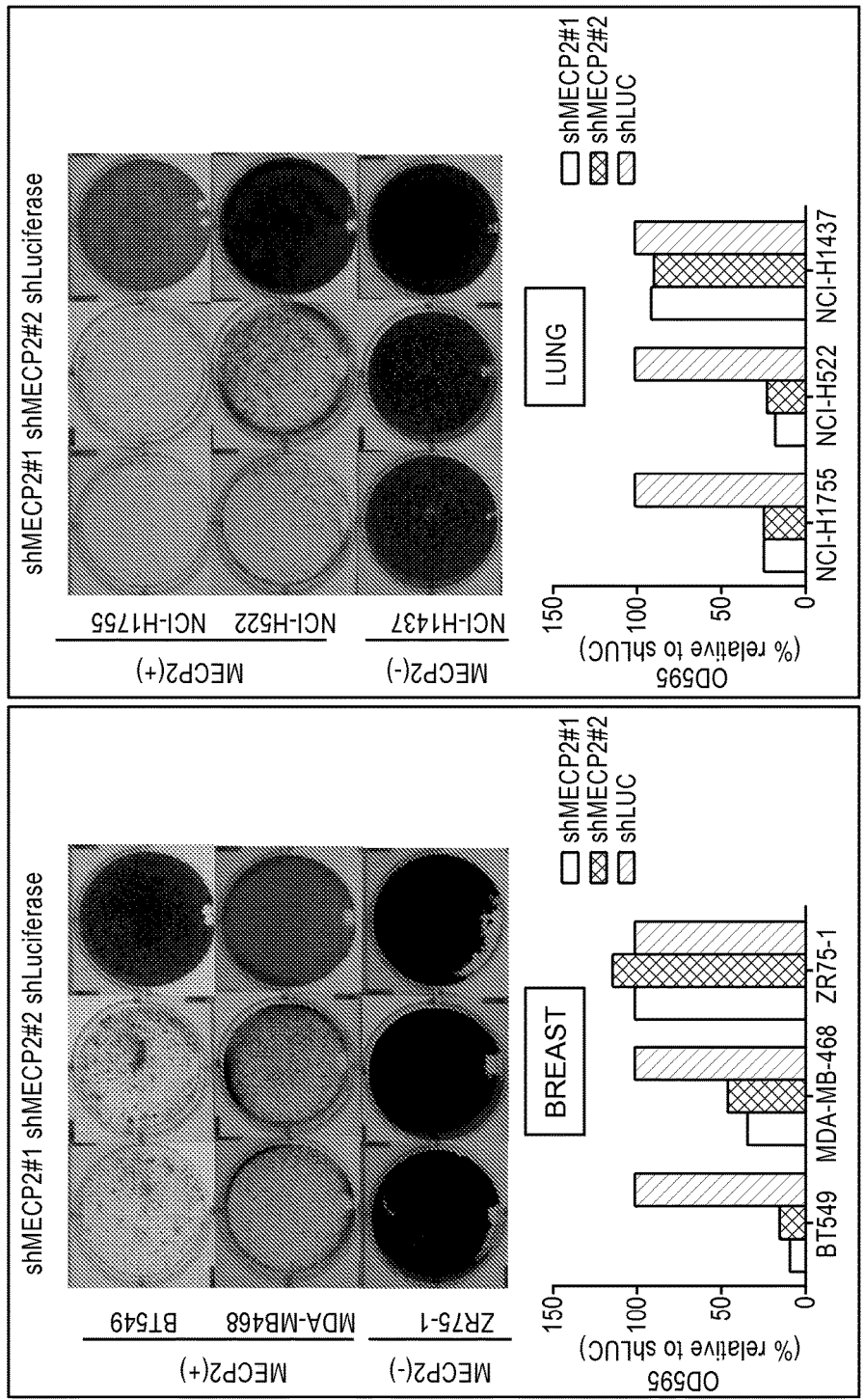
FIG. 19 illustrates that some MECP2 is required for growth in MEPC2 overexpressing cancer cell lines.
Figure 20:
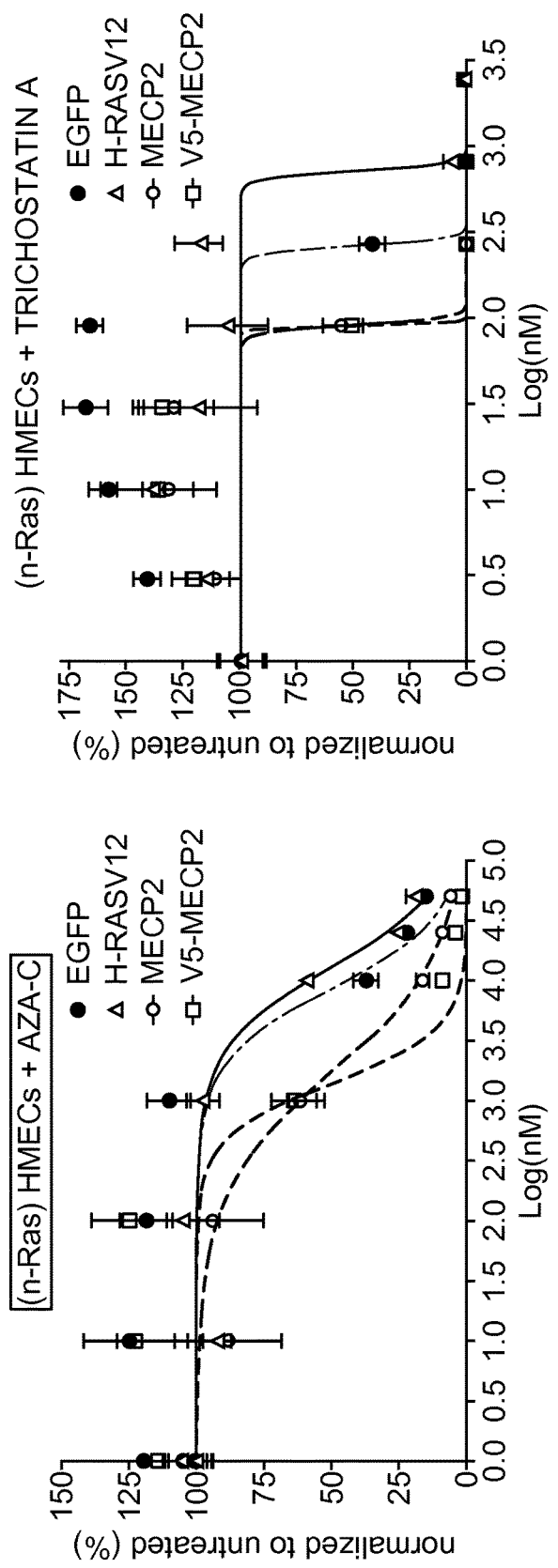
FIG. 20 shows that epigenetic therapies are effective in MECP2-related cancers
Figure 21:
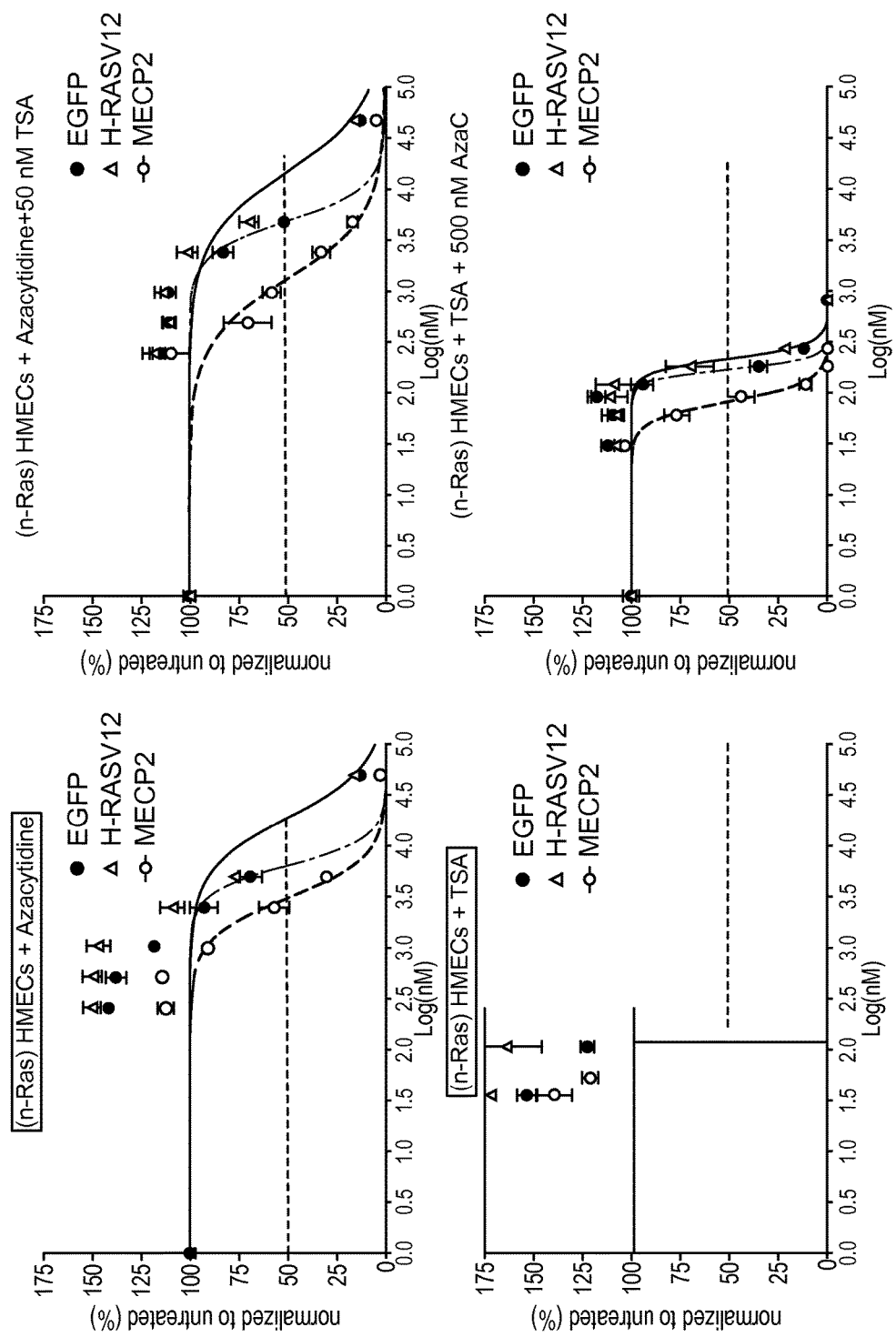
FIG. 21 illustrates the synergistic effect of 5-asacytidine and TSA.
Figure 22:
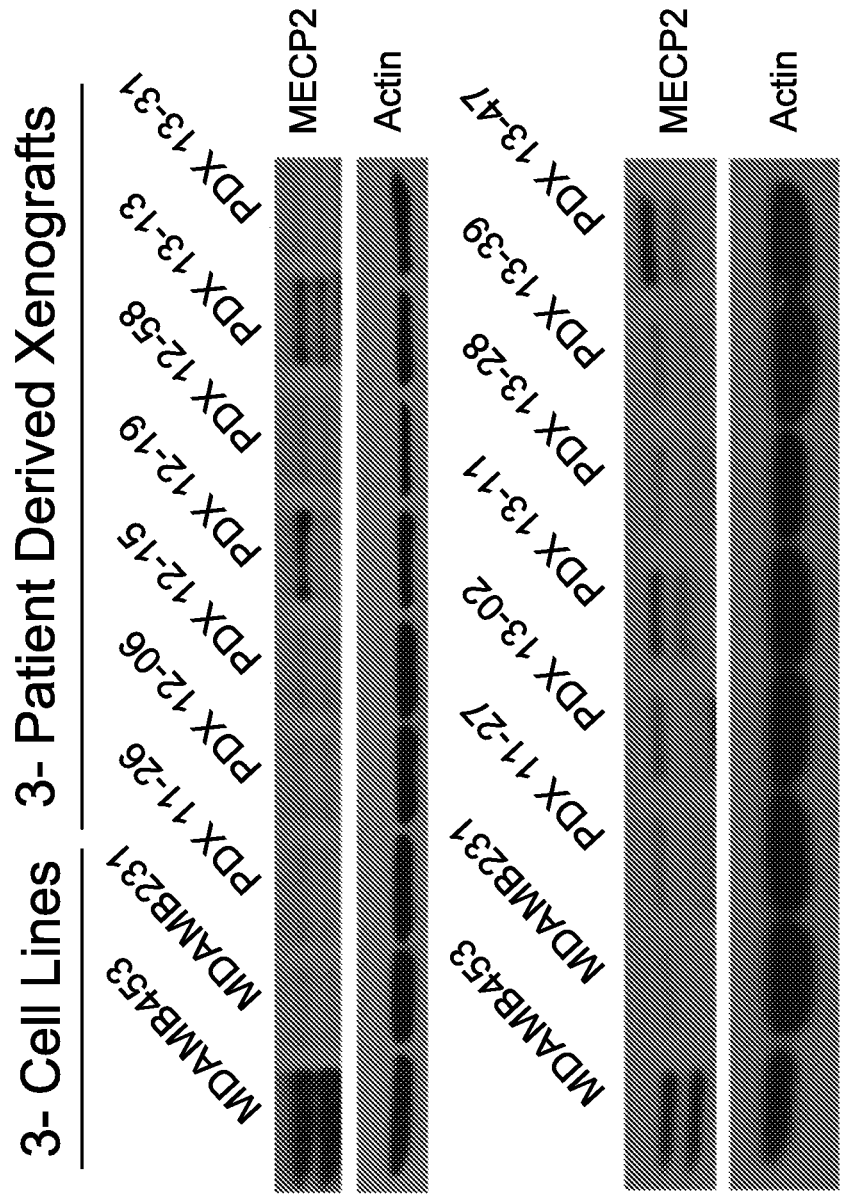
FIG. 22 shows MECP2 expression in triple negative breast cancer (TNBC) patient derived xenografts. MDAMB453 and MDAMB2311 are positive and negative controls for MECP2 overexpression respectively. The remaining samples are patient-derived xenografts (PDXs). PDXs 12-19, 13-13, 13-11 and 13-47 overexpress MECP2.

The present invention relates to the identification of Methyl CpG binding protein 2 (MECP2) as an oncogene. MECP2 is amplified in a number of human cancers such as ovarian cancer and lung adenocarcinomas. Suppression of MECP2 expression significantly inhibits proliferation in several human tumor cell lines that naturally overexpress MECP2, but does not inhibit proliferation of tumor cell lines that do not overexpress MECP2.

The MECP2 gene expresses two splicing isoforms that differ by inclusion of the second exon, resulting in a long isoform that consists of 21 unique amino acids at the amino terminus followed by a 477 amino acid shared region, and a short isoform that has 9 unique amino acids at the amino terminus attached to the same 477aa shared region.

Human cancers harbor innumerable genetic and epigenetic alterations presenting formidable challenges in deciphering those changes that drive the malignant process and dictate a given tumor's clinical behavior. The need for accurately predictive biomarkers reflective of a tumor's response to therapy is evident across many cancer types, Primary human mammary epithelial cells were transformed with three of the four genetic elements of a transformation cocktail (telomerase, SV-40 large T-antigen, SV-40 call T-antigen and RAS) that are required to convert normal primary human cells into tumorigenic cells. Without the fourth component of the transformation cocktail the cells will not grow on soft agar. The lentiviral expression library having about 17,000 different human protein-coding sequences was then inserted into these cells and the cells were plated on soft agar. Genes that could substitute for the fourth component were by identified by isolation of the transduced cDNAs for cell colonies that grew in soft agar. Using this system MECP2 was identified as being sufficient to substitute for activated RAS for tumorgenesis.

As MCEP2 is overexpressed in many human cancers it was hypothesized that MECP2 expression on its own may have the capacity to promote tumor cell proliferation. To test this hypothesis, MECP2 expression was suppressed using shRNA. Suppression of MECP2 expression significantly inhibited proliferation in tumor cells lines that over express MECP2 but not in cells that do not overexpress MECP2. These findings indicate that MCEP2 promote tumor growth.

In addition, these results indicate MECP2 is useful as therapeutic targets for treating MECP2 expressing tumors.

Predicting the Response to Therapy

MECP2 expression is also useful for monitoring subjects undergoing treatments and therapies for cancer, and for selecting or modifying therapies and treatments that would be efficacious in subjects having cancer. The selection and use of such treatments and therapies slows the progression of the tumor, or substantially delays or prevent its onset, or reduces or prevents the incidence of tumor metastasis. In addition, MECP2 is useful as a therapeutic target for treating MECP2 expressing tumors.

The methods disclosed herein are used with subjects undergoing treatment and/or therapies for cancer, subjects who are at risk for developing a reoccurrence of a cancer, and subjects who have been diagnosed with a cancer. The methods of the present invention are to be used to monitor or select a treatment regimen for a subject who has a cancer.

Specifically, the invention provides methods of determining the responsiveness, e.g., sensitivity or resistance, of an individual's tumor therapy. More specifically, the invention provides methods of determining whether a patient with a cancer will be responsive to MECP2 inhibitor therapy by determining whether MECP2 is overexpressed and/or amplified in the tumor. Overexpression and/or amplification of MECP2 indicates that the tumor will be responsive to MECP2 inhibitor therapy. The MECP2 that is overexpressed is the MECP2 long isoform, the MECP2 short isoform or both.

By MECP2 inhibitor therapy it is meant any compound that inhibits the expression or activity of MECP2 such as a nucleic acids that are complementary to a MECP2 nucleic acid, and also included are epigenetic therapies such inhibiting DNA methylation or histone deacetylation. MECP2 inhibitor therapy also includes inhibition of the mitogen-activated protein kinase pathway (MAP2K), tyrosine kinase; c-myc or phosphoinositide 3-kinase (PI3K).

Furthermore, the MECP2 gene expresses two splicing isoforms. The two splicing isoforms can activate different cellular signaling pathways as shown below in Example 1. Expression of the differing isoforms may provide an indication of which MECP2 inhibition therapy is likely to succeed. For example, overexpression of the MECP2 short isoform may best respond to treatment by inhibition of the MAP kinase pathway, whereas overexpression of the MECP2 long isoform may best respond to inhibition of the PI3K pathway.

These methods are both a positive and negative predictive test and thus allow clinicians to better focus the use of these expensive and toxic agents to that subset of the population with the greatest potential chance of benefit as early as possible.

Methods of Treating Cancer

The invention provides methods of treating or alleviating a symptom of cancer by administering to s subject in need thereof a MECP2 inhibitor.

A MECP2 inhibitor is a compound that decreases expression or activity of MECP2.

A decrease in MECP2 expression or activity is defined by a reduction of a biological function of the MECP2. A biological function of MCP2 includes binding to methylated DNA.

MECP2 expression is measured by detecting a MECP2 transcript or protein. MECP2 inhibitors are known in the art or are identified using methods described herein.

The MECP2 inhibitor can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than about 300 daltons, less than about 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

The MECP2 inhibitor is an antibody or fragment thereof specific to MECP2.

Alternatively, the MECP2 inhibitor is for example an antisense MECP2 nucleic acid, a MECP2-specific short-interfering RNA, or a MECP2-specific ribozyme. By the term "siRNA" is meant a double stranded RNA molecule which prevents translation of a target mRNA. Standard techniques of introducing siRNA into a cell are used, including those in which DNA is a template from which an siRNA is transcribed. The siRNA includes a sense MECP2 nucleic acid sequence, an anti-sense MECP2 nucleic acid sequence or both. Optionally, the siRNA is constructed such that a single transcript has both the sense and complementary antisense sequences from the target gene, e.g., a hairpin.

Binding of the siRNA to a MECP2 transcript in the target cell results in a reduction in MECP2 production by the cell. The length of the oligonucleotide is at least 10 nucleotides and may be as long as the naturally-occurring MECP2 transcript. Preferably, the oligonucleotide is 19-25 nucleotides in length. Most preferably, the oligonucleotide is less than 75, 50, 25 nucleotides in length.

Exemplary MECP2 inhibitors include for example a DNA methylation inhibitor (e.g., 5-azacytidine or decitabine), a histone deacetylation (HDAC) inhibitor; a MEK inhibitor, a phosphoinositide 3-kinase (PI3K) inhibitor, a c-myc inhibitor, or a tyrosine kinase inhibitor.

In particular embodiment when the MECP2 short isoform is overexpressed preferred MECP2 inhibitors are MAP kinase inhibitors. In other embodiments when the MECP2 long isoform is overexpressed preferred MECP2 inhibitors are phosphoinositide 3-kinase (PI3K) inhibitors.

The growth of tumor cells is inhibited, e.g. reduced, by contacting a MECP2 overexpressing tumor cell with a composition containing a compound that decreases the expression or activity of MECP2. By inhibition of cell growth is meant the cell proliferates at a lower rate or has decreased viability compared to a cell not exposed to the composition. Cell growth is measured by methods known in the art such as, the MTT cell proliferation assay, cell counting, measurement of ATP content, crystal violet staining, or measurement of total GFP from GFP expressing cell lines.

Cells are directly contacted with the compound. Alternatively, the compound is administered systemically.

The methods are useful to alleviate the symptoms of a variety of cancers. Any cancer exhibiting MECP2 overexpression or amplification is amenable to treatment by the methods of the invention.

Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor. Efficacy is determined in association with any known method for diagnosing or treating the particular tumor type.

Therapeutic Administration

The invention includes administering to a subject composition comprising a MECP2 inhibitor.

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other anti-proliferative agents or therapeutic agents for treating, preventing or alleviating a symptom of a cancer. A therapeutic regimen is carried out by identifying a mammal, e.g., a human patient suffering from a cancer using standard methods.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. The inhibitors are optionally formulated as a component of a cocktail of therapeutic drugs to treat cancers. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically. For example, the compounds are administered by inhalation. The compounds are delivered in the form of an aerosol spray from pressured container or dispenser which contains a suitable propellant, e.g., a gas such as carbon dioxide, or a nebulizer.

Additionally, compounds are administered by implanting (either directly into an organ or subcutaneously) a solid or resorbable matrix which slowly releases the compound into adjacent and surrounding tissues of the subject.

Screening Assays

The invention also provides a method of screening for therapeutic targets (i.e. genes capable of tumorigenic transformation) for treating cancers. In particular, the invention provides a method for identifying therapeutic targets for treating cancer by providing primary cell culture transformed with three of the following genetic elements: telomerase; SV40 large-T antigen; SV40 small-T antigen or RAS and contacting the cell with a library of human protein sequences. Potential therapeutic targets are identified by determining what human protein sequence when expressed in the cell allows for anchorage independent growth.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic, predictive, or prognostic test, assay, or method concerns the ability of the test, assay, or method to distinguish between subjects responsive to chemotherapeutic treatment and those that are not, is based on whether the subjects has an amplification or overexpression of MECP2.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for therapeutic unresponsiveness, and the bottom quartile comprising the group of subjects having the lowest relative risk for therapeutic unresponsiveness. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future events. Often such lower diagnostic accuracy tests must be combined with additional parameters in order to derive meaningful clinical thresholds for therapeutic intervention, as is done with the aforementioned global risk assessment indices.

A health economic utility function is yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

Definitions

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as "clinical parameters" defined herein, as well as "traditional laboratory risk factors", also defined herein. Biomarkers also include any calculated indices created mathematically or combinations of any one or more of the foregoing measurements, including temporal trends and differences. Where available, and unless otherwise described herein, biomarkers which are gene products are identified based on the official letter abbreviation or gene symbol assigned by the international Human Genome Organization Naming Committee (HGNC) and listed at the date of this filing at the US National Center for Biotechnology Information (NCBI) web site.

A "Clinical indicator" is any physiological datum used alone or in conjunction with other data in evaluating the physiological condition of a collection of cells or of an organism. This term includes pre-clinical indicators.

"Clinical parameters" encompasses all non-sample or non-analyte biomarkers of subject health status or other characteristics, such as, without limitation, age (Age), ethnicity (RACE), gender (Sex), or family history (FamHX).

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining biomarkers are linear and non-linear equations and statistical classification analyses to determine the relationship between biomarkers detected in a subject sample and the subject's responsiveness to chemotherapy. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcomes expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested.

See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the responsiveness to treatment, cancer recurrence or survival and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk evaluation" or "evaluation of risk" in the context of the present invention encompasses making a prediction of the probability, odds, or likelihood that an event or disease state may occur, the rate of occurrence of the event or conversion from one disease state. Risk evaluation can also comprise prediction of future clinical parameters, traditional laboratory risk factor values, or other indices of cancer, either in absolute or relative terms in reference to a previously measured population. The methods of the present invention may be used to make continuous or categorical measurements of the responsiveness to treatment thus diagnosing and defining the risk spectrum of a category of subjects defined as being responders or non-responders. In the categorical scenario, the invention can be used to discriminate between normal and other subject cohorts at higher risk for responding. Such differing use may require different biomarker combinations and individualized panels, mathematical algorithms, and/or cut-off points, but be subject to the same aforementioned measurements of accuracy and performance for the respective intended use.

A "sample" in the context of the present invention is a biological sample isolated from a subject and can include, by way of example and not limitation, tissue biopsies, whole blood, serum, plasma, blood cells, endothelial cells, lymphatic fluid, ascites fluid, interstitial fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids. A "sample" may include a single cell or multiple cells or fragments of cells. The sample is also a tissue sample. The sample is or contains a circulating endothelial cell or a circulating tumor cell. The sample includes a primary tumor cell, primary tumor, a recurrent tumor cell, or a metastatic tumor cell.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is considered highly significant at a p-value of 0.05 or less. Preferably, the p-value is 0.04, 0.03, 0.02, 0.01, 0.005, 0.001 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of cancer. A subject can be male or female.

"TN" is true negative, which for a disease state test means classifying a non-disease or normal subject correctly.

"TP" is true positive, which for a disease state test means correctly classifying a disease subject.

"Traditional laboratory risk factors" correspond to biomarkers isolated or derived from subject samples and which are currently evaluated in the clinical laboratory and used in traditional global risk assessment algorithms. Traditional laboratory risk factors for tumor recurrence include for example Proliferative index, tumor infiltrating lymphocytes. Other traditional laboratory risk factors for tumor recurrence known to those skilled in the art.

EXAMPLE 1

Initial Characterization of MECP2 as a New Oncogene

The MECP2 short splicing isoform enables the soft agar growth of primary breast epithelial cells containing introduced SV40 large-T, SV40 small-T, and hTERT with about the same efficiency as activated RAS (FIG. 4A). To assess the potential relevance of MECP2 across all human cancers, a query was made of TCGA copy number data through the Broad Institute TCGA copy number portal. MECP2 is amplified with extremely high statistical significance across all human cancers (FIG. 8) (Q value $7.7 \times 10^{-18}$; Q less than 0.25 signifies likelihood that the gene in question is amplified above the background rate in the genome and that amplifications at this locus are enriched by selective pressure). MECP2 is significantly amplified in a number of individual human cancer types, and is amplified at particularly high frequencies in women's cancers (see FIG. 8).

EXAMPLE 2

Signaling Pathways Activated by MECP2 Splicing Isoforms

To ascertain if MECP2 overexpression recapitulates signal transduction events seen with activated RAS, signaling pathways downstream of RAS were analyzed in N-RAS hMEC cells expressing MECP2 isoforms. The MECP2 gene expresses two splicing isoforms that differ by inclusion of the second exon resulting in a long isoform that consists of 21 unique amino acids at the amino terminus followed by a 477 amino acid shared region, and a short isoform that has 9 unique amino acids at the amino terminus attached to the same 477 amino acid shared region. In most cancers, that have MECP2 amplification, the expression of both isoforms is increased.

Figure 23:
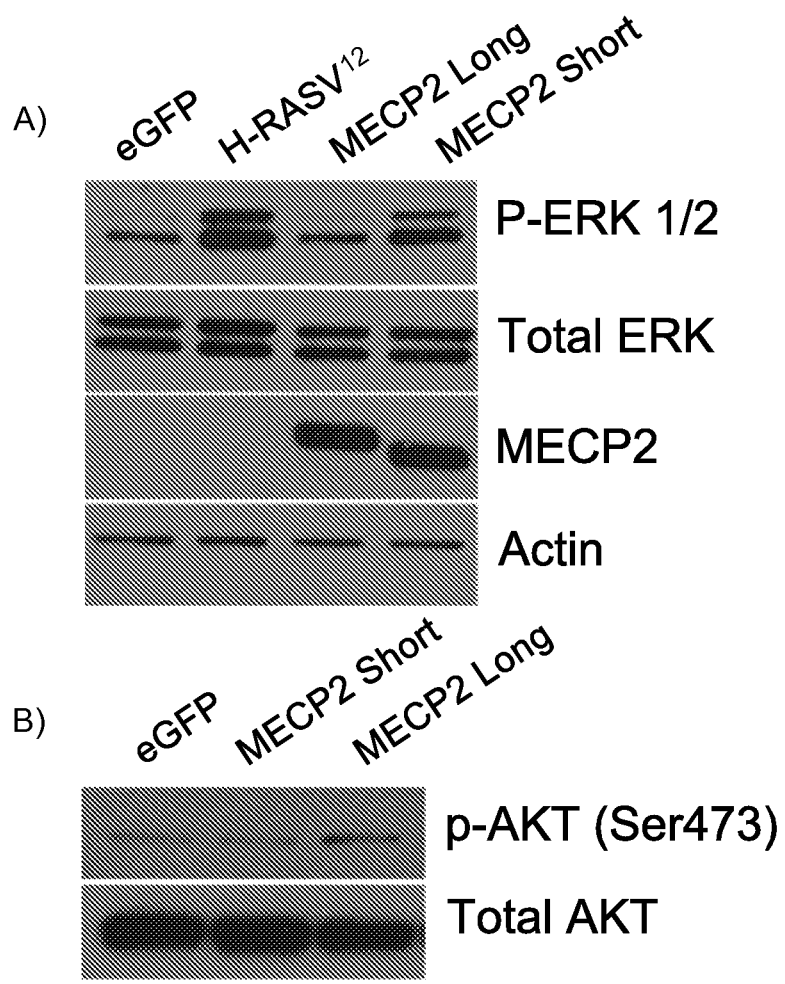
FIG. 23 shows that MECP2 splicing isoforms activate distinct growth factor pathways. hMEC cells contains sv40 small t, SV40 large T, hTERT, and infected with lentiviruses expressing the indicated genes were briefly deprived of growth factors, and lysates prepared were subjected to western blot and probed with the antibodies indicated on the right.

It has been shown that, like activated RAS, overexpression of the MECP2 short isoform causes ERK1/2 phosphorylation (see FIG. 23A), while the MECP2 long isoform activates the PI3K pathway, as monitored by the concentration of phosphorylated AKT (see FIG. 23B). These growth factor pathway activation events were blocked by the presence of mutations in the MECP2 methylated DNA binding region. Supporting the importance of the MAPK pathway, it was demonstrated that two MEK inhibitors with different mechanisms of action significantly slowed the growth of MECP2 transformed cells.

Therefore, in at least one cell type, human mammary epithelial cells, MECP2 short isoform can substitute for activated RAS to confer anchorage independent growth upon human mammary epithelial cells that express the SV40 large-T, SV40 small-t, and hTERT. The MECP2 short isoform includes the MAP kinase pathway to the same extent as activated RAS (see FIG. 23A). The MECP2 short isoform rescues growth of tumor cells addicted to activated RAS after shRNA suppression of RAS. The MECP2 long isoform activates the PI3K pathway (see FIG. 23B).

EXAMPLE 3

MECP2 Causes Tumors in Nude Mice

N-RAS hMECs or N-RAS BPECs do not form tumors in nude mice. It has been shown that in N-RAS hMECs, the combination of both the short and long MECP2 isoforms allow growth as xenografts in nude mice, while each isoform individually does not. BEPCs are intrinsically 1000× more tumorigenic when transformed with SV40LT, st, hTERT and activated RAS compared with hMECs; in N-RAS BPECs, either the long or short isoform of MECP2 is sufficient to cause tumors in nude mice, and the combination of both isoforms gives a higher percentage of tumor takes, and the tumors cause by the combination grow more rapidly than those caused by either isoform alone.

EXAMPLE 4

MECP2 as a Therapeutic Target

Figure 24:
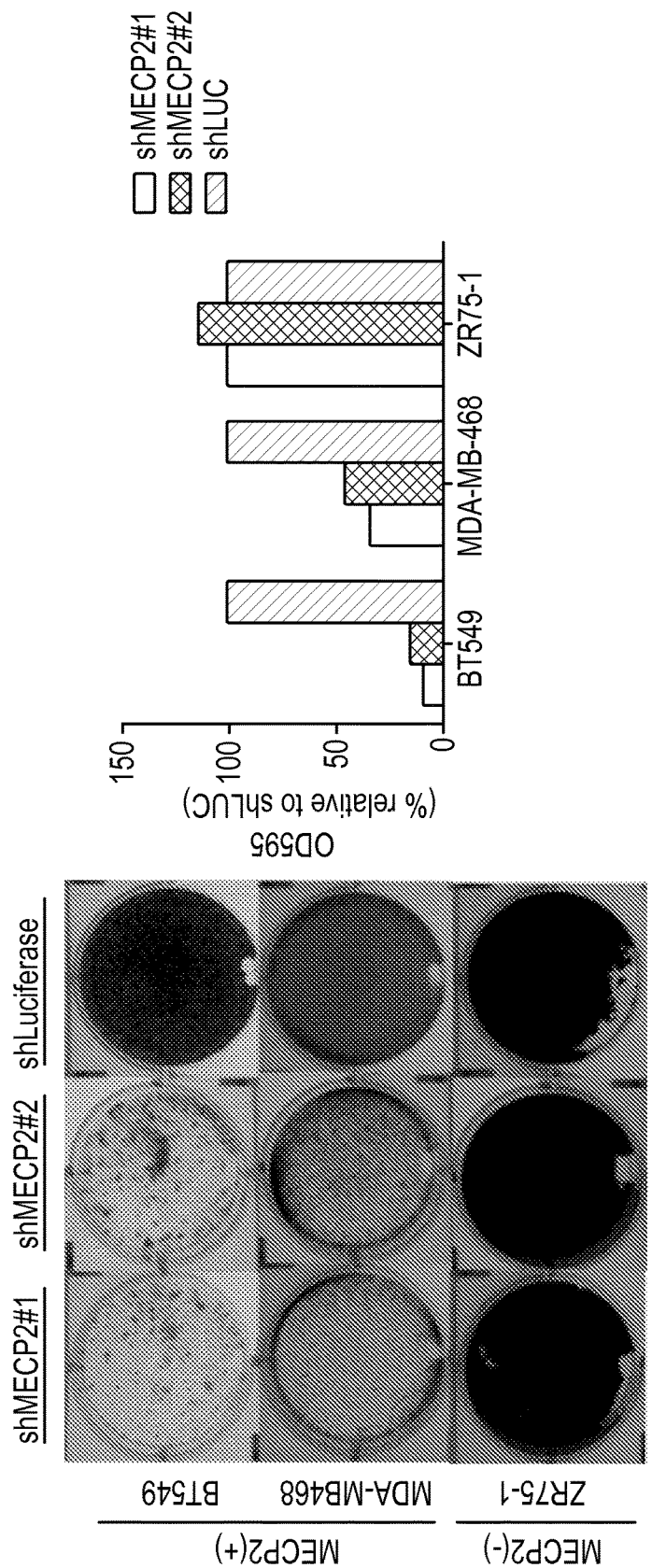
FIG. 24 shows that MECP2 overexpressing TNBC cells are addicted to continued MECP2 expression. MECP2 overexpressing TNBC cell lines BT549 and MDA-MB468 and MECP2 non-overexpressing cell lines ZR75-1 were infected with vectors encoding two different shRNA to MECP2 or Luciferase as a control. Crystal violet staining was done several days later and quantitated by OD595.

In a small survey, it was shown that several TNBC cell lines that overexpress MECP2 require continued MECP2 expression for growth ("oncogene addiction", see FIG. 24) suggesting that MECP2 is a valid therapeutic target in TNBC. These MECP2-overexpressing TNBC lines, BT549 and MDA-MB468, show highly significant growth inhibition when treated with any of three shRNAs (two of which are shown in FIG. 24) directed against MECP2, but not with control shRNA. Breast cancer lines that do not express high levels of MECP2, for example ZR75.1 (see FIG. 9) are not inhibited by these shRNAs suggesting that off-target effects do not cause the growth inhibition observed.

It has been shown that human cancer lines derived from non-small cell lung cancer (NSCLC) and ovarian cancer that overexpress MECP2 are also addicted to continued MECP2 expression for growth, with five shRNAs tested, four against coding regions, one against the 3' UTR, with all showing similar growth inhibition. NSCLC and ovarian cancer cell lines not overexpressing MECP2 were not inhibited by these shRNAs.

Because MECP2 only binds to methylated CpG sequences and hydroxymethylcytosine, and because data have shown that oncogenic activation of MECP2 depends upon its DNA-binding region, it is likely that the oncogenic activity of MECP2 depends upon its DNA-binding region, it is likely that the oncogenic activity of MECP2 is mediated by binding of the protein to methylated CpG sequences of hydroxymethylated cytosine. For this reason, it was investigated whether DNA methylation inhibitors hinder cell growth in a MECP2-dependent manner. DNA methylation inhibitors prevent the formation of both methylated CpG sequences and hydroxymethylated cytosine. It was shown that hMECs transformed with MECP2 are an order of magnitude more sensitive to either of the DNA methylation inhibitors 5-azacytidine or decitabine than are isogenic cells transformed by activated RAS, strongly suggesting that cells transformed in a manner dependent on overexpressed MECP2 are specifically inhibited by 5-azacytidine or decitabine.

MECP2 is known to be present in a complex with Class I histone deacetylases. It was demonstrated that the region of MECP2 required for binding to HDACs is also required for the transformation activity of MECP2. This led to investigation of whether MECP2-transformed cells were particularly vulnerable to HDAC inhibitors. MECP2-transformed cells are an order of magnitude more susceptible to the HDAC inhibitor Trichostatin A than are isogenic cells transformed by activated RAS. Furthermore, it was shown that combined treatment with the DNA methylation inhibitor 5-azacytdine and the HDAC inhibitor Trichostatin A is synergistic in a hMEC experimental system.

We claim:

1. A method of treating a subject having a breast cancer, lung cancer, or ovarian cancer, wherein the cancer has an MECP2 amplification or overexpression of MECP2, the method comprising administering to the subject a MECP2 inhibitor, a DNA methylation inhibitor, a histone deacetylation (HDAC) inhibitor, a MEK inhibitor, a phosphoinositide 3-kinase (PI3K) inhibitor, a c-myc inhibitor, a tyrosine kinase inhibitor or any combination thereof.

2. The method of claim 1, wherein the MECP2 is the long isoform and the MECP2 inhibitor is a phosphoinositide 3-kinase (PI3K) inhibitor.

3. The method of claim 1, wherein the MECP2 is the short isoform and the MECP2 inhibitor is a MAP kinase inhibitor.

4. The method of claim 1, further comprising administering to the subject a HDAC inhibitor.

5. The method of claim 1, wherein the DNA methylation inhibitor is 5-azacytidine or decitabine.

6. The method of claim 1, wherein the DNA methylation inhibitor is administered locally or systematically.

* * * * *